(12) United States Patent
Guyer et al.

(10) Patent No.: US 9,255,199 B2
(45) Date of Patent: *Feb. 9, 2016

(54) HYDROPHILIC SILICONE MONOMERS, PROCESS FOR THEIR PREPARATION AND THIN FILMS CONTAINING THE SAME

(71) Applicant: Momentive Performance Materials, Inc., Waterford, NY (US)

(72) Inventors: Kendall Louis Guyer, Bartlett, IL (US); Kenrick Martin Lewis, Flushing, NY (US); Senthilkumar Umapathy, Bangalore (IN); Anubhav Saxena, Bangalore (IN); Yi-Feng Wang, Clifton Park, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/182,709

(22) Filed: Feb. 18, 2014

(65) Prior Publication Data

US 2014/0163135 A1    Jun. 12, 2014

Related U.S. Application Data

(63) Continuation of application No. 13/122,255, filed as application No. PCT/IN2009/000550 on Oct. 5, 2009, now Pat. No. 8,686,099.

(60) Provisional application No. 61/195,086, filed on Oct. 3, 2008.

(51) Int. Cl.
| | |
|---|---|
| C08L 33/14 | (2006.01) |
| C07F 7/08 | (2006.01) |
| C07F 7/21 | (2006.01) |
| G02C 7/04 | (2006.01) |

(52) U.S. Cl.
CPC ............... *C08L 33/14* (2013.01); *C07F 7/0852* (2013.01); *C07F 7/21* (2013.01); *G02C 7/04* (2013.01)

(58) Field of Classification Search
None
See application file for complete search history.

(56) References Cited

U.S. PATENT DOCUMENTS

| | | | | |
|---|---|---|---|---|
| 4,136,250 | A | * | 1/1979 | Mueller et al. .................. 528/29 |
| 4,152,508 | A | * | 5/1979 | Ellis et al. ..................... 526/279 |
| 4,224,427 | A | * | 9/1980 | Mueller et al. .................. 526/93 |
| 4,235,985 | A | * | 11/1980 | Tanaka et al. ................. 526/279 |
| 4,259,467 | A | | 3/1981 | Keogh et al. |
| 4,260,725 | A | * | 4/1981 | Keogh et al. .................. 526/279 |
| 4,330,383 | A | * | 5/1982 | Ellis et al. ..................... 526/279 |
| 4,508,884 | A | * | 4/1985 | Wittmann et al. ............. 526/279 |
| 5,969,076 | A | * | 10/1999 | Lai et al. ......................... 528/28 |
| 8,486,188 | B2 | * | 7/2013 | Jaunky et al. ............ 106/287.14 |
| 8,686,099 | B2 | * | 4/2014 | Guyer et al. .................. 526/279 |
| 2009/0299022 | A1 | * | 12/2009 | Ichinohe ....................... 526/279 |

FOREIGN PATENT DOCUMENTS

JP    2008-202060    9/2008

OTHER PUBLICATIONS

Chinese Office Action dated Jul. 2, 2013 for Chinese Application No. 200980139434.7.
ISA/US, International Search Report and Written Opinion, for PCT/IN09/00550 owned by Momentive Performance Materials Inc. dated Oct. 5, 2009.
Korean Office Action for Korean Patent Application No. 10-2011-7007578, mailed Aug. 20, 2015.

* cited by examiner

*Primary Examiner* — Peter A Salamon
(74) *Attorney, Agent, or Firm* — Joseph E. Waters, Esq.; McDonald Hopkins LLC

(57) ABSTRACT

There is provided new mono-(meth)acrylate functionalized hydrophilic silicone monomers containing a polyether with branched linking group, useful in making water absorbing silicone-hydrogel films for contact lens applications. This invention also provides homo-polymers and copolymers made from the mono-(meth)acrylate functionalized hydrophilic silicone monomers described herein. Also provided is a process for producing the monomers and polymers described herein and contact lenses produced from the same.

22 Claims, No Drawings

HYDROPHILIC SILICONE MONOMERS, PROCESS FOR THEIR PREPARATION AND THIN FILMS CONTAINING THE SAME

FIELD OF THE INVENTION

The present invention relates to mono-functional hydrophilic silicone-containing monomers having a polyether with branched linking group, and homo and copolymers produced therefrom. The present invention also relates to a process for producing the hydrophilic silicone-containing monomers and polymers of the present invention. Still further, the present invention is directed to hydrogel compositions useful for the production of biomedical devices, especially contact lenses.

BACKGROUND OF THE INVENTION

Silicone-hydrogel films are used to make extended wear soft contact lenses due to their high oxygen permeability, flexibility, comfort and reduced corneal complications. Conventional hydrogel materials (e.g. 2-hydroxyethylmethacrylate, HEMA) by themselves have poor oxygen permeability and they transport oxygen to the eye through the absorbed water molecules. Water has low oxygen permeability, also called the Dk value, which may be expressed in Barrer, wherein 1 Barrer=$10^{-11}$ (cm$^3$ O$_2$) cm cm$^{-2}$ s$^{-1}$ mmHg$^{-1}$ where 'cm$^3$ O$_2$' is at a quantity of oxygen at standard temperature and pressure and where 'cm' represents the thickness of the material and cm$^{-2}$ is the reciprocal of the surface area of that material. The Dk of water is 80 Barrer. These lenses upon exposure to atmospheric air for longer periods are slowly dehydrated and the amount of oxygen transported to the cornea is reduced. Eye irritation, redness and other corneal complications can result and hence restrict use of the lenses to limited periods of wear.

Silicone-hydrogels with the comfort of soft contact lenses and significantly higher oxygen permeability overcame the obstacles for periods of wear beyond conventional hydrogels and were revolutionary in the field of optometry. The following patents describe silicone-hydrogels for use in contact lenses.

U.S. Pat. No. 4,260,725 to Bausch & Lomb Inc describes a water absorbing, soft, hydrophilic, flexible, hydrolytically stable, biologically inert contact lens with the capability of transporting oxygen sufficiently to meet the requirements of the human cornea comprising a polysiloxane which is $\alpha,\omega$ terminally bonded through divalent hydrocarbon groups to polymerizably activated unsaturated groups and which contain hydrophilic sidechains.

U.S. Pat. No. 5,352,714 also to Bausch & Lomb Inc. describes silicone-containing hydrogels with enhanced wettability comprising a silicone-containing monomer, hydrophilic monomers, and a relatively non-polar ring-containing monomer able to be converted to a highly polar amino acid upon hydration.

U.S. Pat. No. 5,998,498 to Johnson & Johnson Vision Products describes a silicone hydrogel prepared by curing a reaction mixture comprising a silicone-containing monomer having the following structure:

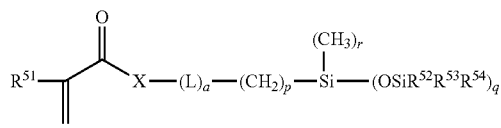

wherein $R^{51}$ is H or CH$_3$, q is 1 or 2 and for each q, $R^{52}$, $R^{53}$ and $R^{54}$ are independently ethyl, methyl, benzyl, phenyl or a monovalent siloxane chain comprising from 1 to 100 repeating Si—O units, p is 1 to 10, r=(3−q), X is 0 or NR$^{55}$, where R$^{55}$ is H or a monovalent alkyl group with 1 to 4 carbons, a is 0 or 1, and L is a divalent linking group which preferably comprises from 2 to 5 carbons, which may also optionally comprise ether or hydroxyl groups, for example, a polyethylene glycol chain.

U.S. Pat. No. 6,867,245 to Asahikasei Aime Co. describes a soft contact lens, and provides a contact lens which shows small and stable contact angle to water at its surface in water as well as in air, little deposition in wearing, high oxygen permeability, no adhesion of lens to a cornea and superior extended-wearing characteristics. It describes a hydrogel soft contact lens, which has contact angle at a lens surface in a range of 10-50° by the captive bubble method in water and 3 & 90° by the sessile drop method in air, oxygen permeability of not less than 30 and water content of not less than 5%, and also a hydrogel soft contact lens consisting of a polymer comprising a hydrophilic siloxanyl monomer shown by a specified general formula. This patent discloses copolymers of hydrophilic siloxane with amide-group containing monomers that are stated as being useful materials for contact lenses. The polymer comprises hydrophilic amide-group containing siloxanyl methacrylate, a siloxanyl methacrylate (tris[trimethylsiloxy] silylpropylmethacrylate, abbreviated as TRIS) including a hydrophilic polyether modified siloxanyl alkyl methacrylate and a crosslinkable monomer.

U.S. Pat. No. 6,013,711 to the CK Witco Corporation describes a method for improving the miscibility of the lower molecular weight unsaturated siloxane-polyether copolymers with the $\alpha,\omega$-divinylpolysiloxanes without loss of storage stability, or delay of cure at the vulcanization temperature, or loss of permanent hydrophilicity or other desirable features of the cured polysiloxane. The compositions comprise one or more $\alpha,\omega$-divinylpolysiloxanes, unsaturated polysiloxane-polyether copolymers having from 2 to 5 silicon atoms per molecule, which are preferably trisiloxanes, and a compatibilizing additive. The permanently hydrophilic, rapidly wettable polysiloxane compositions yield static water contact angles <50° and dynamic advancing contact angles of less than about 100.

U.S. Pat. No. 6,207,782 to Crompton Corporation discloses acrylated hydrophilic polysiloxanes monomers and polymers and their copolymers with acrylate/methacrylate comonomers and their emulsions for personal care, textile and coating applications. The acrylated siloxanes are represented by formula a

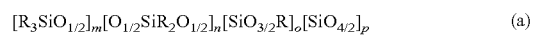

wherein R is selected from the $R^1$ and P, wherein each $R^1$ can be the same or different and each is a monovalent hydrocarbon group; each P is $R^3[O(C_bH_{2b}O)_zCOCR^4=CH_2]_g$ wherein, $R^3$ is a polyvalent organic moiety, which may be hydroxy substituted alkylene, g is the valency of $R^3$ minus 1, $R^4$ is hydrogen or methyl; b=2 to 4, preferably 2 to 3; z=1 to 1000, preferably 3 to 30; and m+n+p+o=1 to 100, preferably 2 to 20, at least one R is P; n=1 to 100; when o is not zero n/o <10:1; when p is not zero n/p <10:1; and m=0 to 10. A preferred acrylated siloxane of the invention is of the Formula (b)

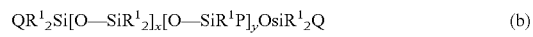

wherein x, and y can be 0 or an integer, preferably each x and y are from 0 to 100, most preferably 0 to 25; Q can be $R^1$ or P, with the proviso that the average acrylate functionality is >1 unsaturated groups per molecule. In the preferred embodiment y=0 and Q=P.

Conventionally, silicone-hydrogels are made by polymerizing the acrylate or methacrylate functionalized silicone monomer with hydrogel (hydrophilic) monomers, such as hydroxyethyl methacrylate (HEMA), N-Vinylpyrrolidone (NVP) and other monomers such as methyl methacrylic acid (MA), Dimethylacrylamide (DMA), etc, in the presence of crosslinker and free radical or photoinitiators. Crosslinking agents generally have two or more reactive functional groups at different sites of the molecule. Typically, these sites contain polymerizable ethylenic unsaturation groups. During curing, they form a covalent bond with two different polymer chains and form a stable three-dimensional network to improve the strength of the polymer. Crosslinking agents conventionally used in contact lenses include ethylene glycol dimethacrylate and trimethyloylpropane trimethacrylate (about 0.1 to 2 wt %). Other useful crosslinking agents include diethyleneglycol dimethacrylate, bisphenol A dimethacrylate, diglycidyl bisphenol A dimethacrylate and dimethacrylate-terminated polyethylene glycol and reactive linear polyether modified silicones.

Generally, silicone hydrogel contact lens materials are made using either hydrophobic mono-functional silicone monomer (such as TRIS) or multi-functional hydrophilic, silicone monomer followed by secondary surface treatment. Mono-functional silicone monomers are preferred in the contact lens industry over multi-functional silicone monomers since the latter lead to increased rigidity of the lens made therefrom.

Although the state of this art for soft contact lenses has been improving, the silicone-based materials described in these patents still possess major shortfalls, like sub-optimal surface wettability and lipid deposition. In an effort to overcome these drawbacks, current state of the art technology uses either expensive secondary surface treatments called 'plasma oxidation' or use internal wetting agents at the expense of oxygen permeability. Hence there remains a need for hydrophilic silicone monomers with inherently advantageous wettability and oxygen permeability that can be used to make contact lenses without the drawbacks and expensive surface treatments necessary with the silicone containing materials of the present art.

Hydrosilylation synthesis of siloxane-polyether copolymers with alkyl branched unsaturated polyethers, such as methylallyl polyethers, is known in the art. See for example, U.S. Pat. No. 3,507,923 and U.S. Pat. No. 4,150,048. However, the realization of improved oxygen permeability and water wettability in polymer films prepared from acrylate and methacrylate capped derivatives of these siloxane-polyether copolymers is novel. Accordingly, the present invention discloses new mono-acrylate or methacrylate functionalized silicone monomers containing a polyether moiety with a branched linking group, processes to produce such monomers with high purity and ease of manufacturability and homo and copolymers made from these monomers that have greater hydrophilic functionality. These functionalized silicone monomers are useful to make water-absorbing, oxygen-permeable silicone-hydrogel films that can be fashioned into extended wear soft contact lens. In particular, the monomers disclosed in the current invention have a branched linking group, which connects the siloxane unit with the polyalkyleneoxide block terminally functionalized with a reactive methacrylate group. Silicone hydrogel films produced with these monomers offer improved surface wettability, oxygen permeability and mechanical properties in comparison to silicone-hydrogel films prepared from monomers having linear alkyl linking groups, such as those already disclosed in the prior art for contact lens applications.

BRIEF SUMMARY

In one aspect, there is provided a silicone monomer having the general formula (I) or (II)

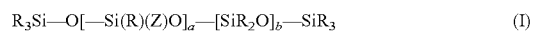

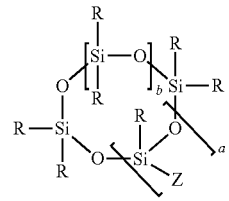

wherein a is 1 to 50; b is 0 to 100; each R is independently selected from the group consisting of monovalent aliphatic, cycloaliphatic or aromatic hydrocarbon groups of 1 to about 10 carbons and halogenated hydrocarbon groups of 1 to about 10 carbons, and Z is a polyether moiety having a branched alkyl group having the general Formula (III):

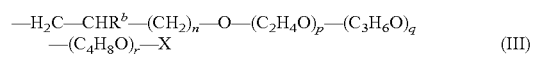

wherein
n is 1 to about 20; p and q are independently 0 to about 100; r is 0 to about 50 and (p+q+r) is greater than 0; $R^b$ is an alkyl group having from 1 to about 4 carbon atoms, X is a polyether-capping group having the general formula (IV):

wherein $R^3$ and $R^4$ independently are either hydrogen or a substituted or unsubstituted saturated mono-valent hydrocarbon group of 1 to about 20 carbons.

The present invention also provides homo and copolymers derived from the described monomers and silicone hydrogels containing the same.

The present invention also describes a process for producing the described monomers by reacting a silicone-containing compound having the general formula (V)

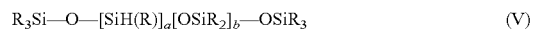

wherein a is 1 to 50; b is 0 to 100; each R is independently selected from the group consisting of monovalent aliphatic, cycloaliphatic or aromatic hydrocarbon groups of 1 to about 10 carbons and halogenated hydrocarbon groups of 1 to about 10 carbons;
with a polyether having at least one end terminated with hydroxyl or halogen or epoxy and the other end terminated with a branched alkene, and having the general formula (VI):

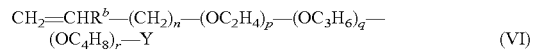

wherein n is 1 to about 20, p and q are 0 to about 100; r is 0 to about 50; $R^b$ is an alkyl group having from 1 to about 4 carbon atoms, Y is OH, halogen or an epoxy group to produce a polyether siloxane and then reacting said polyether siloxane with an alkylacryloyl compound having the general formula (VII):

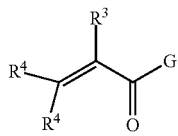

(VII)

wherein G is a halogen or —OH and $R^3$ and $R^4$ independently are either hydrogen or a hydrocarbon group of 1 to about 10 carbons to produce said silicone monomer.

DETAILED DESCRIPTION OF THE INVENTION

In accordance with the present invention, new mono-(meth)acrylate functionalized hydrophilic silicone monomers having a polyether moiety containing a branched linking group and useful for preparing water-absorbing silicone-hydrogel films for contact lens applications are described. Silicone hydrogel films obtained with these monomers show better surface wettability, oxygen permeability and desirable modulus in comparison to previously disclosed films made from the corresponding silicone polyether monomers having linear alkyl linking groups. The novel monomers disclosed have a branched linking group in the polyether moiety, which makes it possible to produce hydrophilic polyether modified silicone copolymers without the need to separate unreacted, isomerized polyether and associated high molecular weight by-products.

In the present invention, the alkyl group, which connects the silicone unit to the hydrophilic polyether chain, is a substituted alkyl group that prevents isomerization of the unsaturated polyether during synthesis. The presence of the branched linking group allows greater purity of the silicone-polyether copolymer taken directly from a reactor. In addition, and quite surprisingly, silicone-hydrogel films produced using the present silicone-polyether copolymers with branched linking groups show improved oxygen permeability, low water contact angles (very good surface wettability) and moduli that facilitate lens removal and insertion and that contribute to comfort when lens are worn. These are distinct improvements when compared to silicone-polyether copolymers having linear alkyl linking groups.

The monomers of the present invention are also miscible with hydrophilic co-monomers without the need for any homogenizing solvent, thereby affording silicone hydrogels that are transparent across the entire range of monomer-co-monomer compositions.

Optimal miscibility (optimal solubility parameter) of the silicone monomer with different organic monomers is achieved by changing either or both the chain length of a polyether (hydrophile) or the ratio of alkylene oxides (for example ethylene oxide and propylene oxide) in the polyether chain. If the polyether chain is too short or too long, of the wrong average polarity, or absent, then miscibility with common unsaturated organic monomers may be poor and lead to opaque materials. Miscibility of silicone-polyether copolymers with unsaturated silicone reactants, solvents and polymers useful for the production of contact lens polymers is also similarly influenced. The size and structure of the silicone group can also be independently varied to influence miscibility, but if the amount of silicone relative to polar functional groups is too large, then the organosilicone monomer will be immiscible with polar organic monomers.

In the specific instance that b is zero in formula (I) or (II) above, miscibility with 2-hydroxyethylmethacrylate (HEMA) can be achieved with a Z group of the type: —$CH_2$—$CH_2$—$CH_2$—O—$CH_2$—$CH_2$—$OCH_2$—$CH_2$—OR where at least two ethylene oxide units are present. A reason for this is that the miscibility of these silicone monomers represented by Formula (I) or (II) with polar co-monomers such as 2-hydroxyethylmethacrylate (HEMA) is controlled by the ratio of the silicone moiety to the polar polyether group in the silicone monomer. If no polyether, or too little polyether, is in the silicone monomer, then the silicone monomer is immiscible with HEMA and solvent is required to homogenize them.

Conversely, if too little silicone is present in a silicone-polyether copolymer the desired characteristic of enhanced oxygen transport in a contact lens polymer may be diminished. The materials of the invention are actually distributions of compositions resulting from the underlying chemistry of the manufacture of silicone and polyether precursors that are themselves distributions of components. It may be desirable to control the nature of the distribution by chemical and/or physical processes that can remove or reduce the amount of a component or range of components in a distribution that would be less miscible with a particular set of monomers and other constituents in a formulation used to make a contact lens polymer.

Purification of the silicone and/or polyether reactants by distillation, high vacuum stripping, preparative chromatography or supercritical fluid extraction can be used to control the final copolymer distribution. Where small polyether reactants (number average of ether units in the polyether from about two to about six) are to be used to prepare a silicone-polyether copolymer, the removal of the alcohol starter and a single alkylene oxide adduct (that is the starter alcohol reacted with only one alkylene oxide unit) from the distribution is of interest. A purified polyether precursor where unreacted alcohol starter and single alkylene oxide adducts have been removed by distillation or high vacuum stripping, as non-limiting examples, is useful since it could be used as the starter to make short chain (about two to about six) polyether without zero or single ether adducts being present in concentrations that would interfere with a formulation used to produce a contact lens polymer. Treatment of the polyether with ascorbic acid and ascorbates as described in U.S. Pat. No. 5,986,122 improves its hydrosilylation reactivity.

As used herein, "homopolymers" are polymers made from the same repeating monomer and 'copolymers" are polymers wherein the polymer contains at least two structurally different monomer units. Monomers and polymers with linear alkyl linked (meth)acrylated silicone polyether chains means those compounds without any branching in the linking group that connects the siloxane with the polyalkylene oxide part of the side chain in such compounds. Notations such as (meth)acrylate denote monomer with either acrylate or methacrylate functionality. The monomers of the present invention can be used to obtain cured elastomers with desirable physical strength and resistance to tearing after absorption of water. The mono-(meth)acrylate functionalized silicone monomers/polymers of the present invention and their preparation and use in contact lens are further described in the sections below.

The present invention also provides silicone-hydrogel compositions comprising (meth)acrylate functionalized hydrophilic silicone monomer and conventional monomer such as HEMA or other contact lens monomers to produce soft, flexible water absorbing films. The homo and copolymers of the present invention are clear (no haze from poor miscibility) polymers that absorb about 10 wt. % to about 60 wt. % of water, showing excellent surface wettability and effective oxygen permeability, all of which are necessary for the better comfort when lens are worn and for good health of the human cornea. The present invention also provides contact lenses made from the silicone-hydrogel films of the claimed invention. These embodiments are further described below.

The monomers with high molecular weight polyether chains produced in the current invention may be used to form hydrophilic silicone homo/copolymers that produce silicone-hydrogel films having better oxygen permeability and significantly improved surface wettability in comparison to monomers with linear alkyl linking groups in the polyether chains. The contact lenses produced from the silicone-hydrogel films of the present invention do not require any expensive secondary treatments, like plasma oxidation or plasma coating, or internal wetting agents to improve wettability. That is, the contact lenses produced from silicone-hydrogel films of the present invention, without secondary treatment, are soft, flexible and inherently wettable and exhibit high oxygen permeability.

The monomers of the present invention can be pendant (comb-like) or cyclic with the general formula (I) for pendant structures:

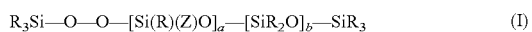
(I)

which can be depicted structurally as:

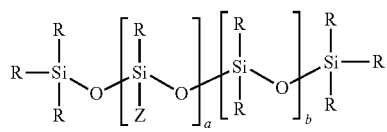

and with the general formula (II) for the cyclic structures being:

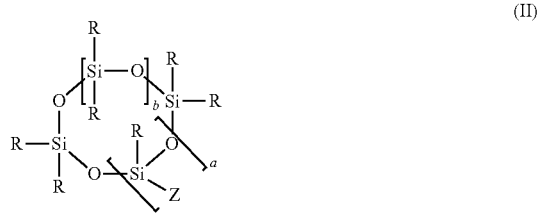
(II)

wherein, for both structures, a is 1 to about 50; b is 0 to about 100; each R is independently selected from the group consisting of monovalent aliphatic, or cycloaliphatic hydrocarbon groups of 1 to about 10 carbons, preferably 1 to about 6 carbons, or an aromatic hydrocarbon groups of from 1 to about 10 carbons, preferably phenyl, or a halogenated hydrocarbon group of 1 to about 10 carbons, preferably a fluoro hydrocarbon.

In the general formulas for the monomer cited above, Z is a polyether with branched alkyl group having the general formula (III):

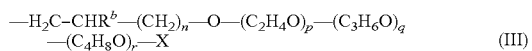
(III)

which can be depicted structurally as:

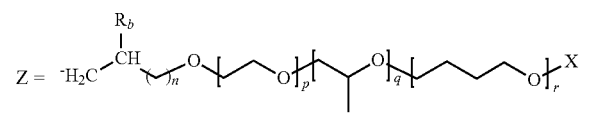

wherein n is 1 to about 20; p and q are 0 to about 100; r is 0 to about 50 and (p+q+r) is greater than 0; and $R^b$ is an alkyl group of from 1 to about 4 carbon atoms, preferably —CH$_3$, X is a polyether-capping group represented having the general formula (IV)

(IV)

wherein $R^3$ and $R^4$ independently are either hydrogen or a substituted or unsubstituted saturated monovalent hydrocarbon group of 1 to about 20 carbons. In the specific instance that b is zero in the monomer formulas above, then the total number of carbon atoms in the polyether group Z is preferably 6 or greater.

As noted above, the inventive monomers of the present invention may be cyclic. For cyclic monomers of the present invention, the terminal silicon atoms are linked together by an oxygen atom with total (a+b) value is preferably between about 1 and 20 for the linear structure and 3 to about 20 for the cyclic structure.

The present invention is also directed to polymers formed by the reaction products of the present inventive monomers. These polymers may be homopolymers of one of the monomers of the present invention or copolymers of two structurally different silicone monomers of the present invention and/or copolymers of one or more silicone monomers of the present invention and at least one other hydrophilic unsaturated organic monomer suitable for use in silicone hydrogels, with preferred non-limiting examples of such being N,N-dimethylacrylamide, 2-hydroxy-ethyl-methacrylate (HEMA), N-vinylpyrrolidone, and methacrylic acid. In such copolymers, the copolymer ratio of the silicone monomer of the present invention to the other hydrophilic unsaturated organic monomers is from 1:100 to about 100:1.

To form polymers using the monomers of the present invention, the desired monomers are mixed and the resulting mixture is polymerized and cured to form transparent thin films by known thermal or UV cure techniques, using either peroxides or photoinitiators in the presence of crosslinking agents. The monomers added to the monomer mix to create the mixture prior to polymerization to form the polymers may be monomers or prepolymers. A "prepolymer" is a reaction intermediate polymer of medium molecular weight having polymerizable groups. Thus it is understood that the terms "silicone-containing monomers" and "hydrophilic monomers" include prepolymers. The present invention is also directed to silicone hydrogel films comprising the homopolymers or copolymers detailed above.

One preferred silicone monomer of the present invention has the following formula

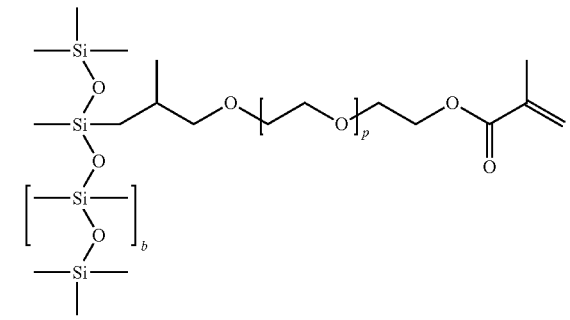

wherein p is 1 to about 50, preferably 2 to about 15, more preferably about 8, and b is 0 to about 100, more preferably 0 to 2 inclusive, and even more preferably 0. $R^b$ and each of the R groups in the general monomer structure are methyl groups in this preferred monomer.

In another embodiment, the present invention is also directed to a process for producing the described silicone monomers comprising chemically reacting a silicone-containing compound having the general formula (V):

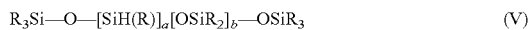
(V)

wherein a, b, and R are defined above; with at least one hydroxyl, halogen or epoxy capped, alkyl branched unsaturated polyether having the general formula (VI):

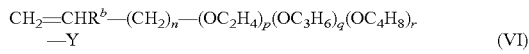
(VI)

Which can be depicted structurally as:

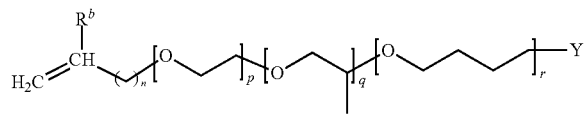

wherein n is 1 to about 20, preferably 2 to about 16 and more preferably 2 to about 6; p and q are individually 0 to about 100; r is 0 to about 50; $R^b$ is an alkyl group attached to the beta carbon of a terminal alkene group, Y is OH, a halogen or an epoxy; in the presence of a catalyst to produce a polyether siloxane, and then reacting said polyether siloxane with an alkylacryloyl compound having the general formula (VII):

(VII)

wherein G is a halogen or —OH and $R^3$ and $R^4$ are independently either hydrogen or a hydrocarbon group of 1 to about 10 carbons, in the presence of a base to produce said silicone monomer. $R^3$ is preferably a methyl group and $R^4$ is preferably hydrogen. The reaction of the polyether siloxane with alkylacryloyl compound having the general formula (VII) can be carried out in the presence of a tertiary amine base or basic ion-exchange resin (IER) and a low boiling point solvent. Trialkyl amines, such as triethyl amine and tripropyl amine, are suitable bases. The solvent used can be selected from hexane, methylethylketone, acetone, dichloromethane, chloroform or other low boiling point solvents with similar solubility parameter and inertness under the reaction conditions.

A particular embodiment of the present invention is directed to the above-described process wherein, for the formulas above, R and $R^b$ are methyl groups, b is 0, q and r are 0; p is 0 to about 100, preferably 0 to about 50 and more preferably 0 to about 10 and Y is OH, G is chlorine or OH.

The hydrosilylation reaction of compounds of general formula (V) with those of general formula (VI) can be carried out with or without solvents and additives as described in U.S. Pat. Nos. 3,229,112; 4,847,398; 4,857,583; 5,191,103; or 5,159,096, relevant portions of which are incorporated herein by reference. A major advantage attendant to the selection of the alkyl branched, unsaturated polyether (general formula (VI)) is the use of substantially stoichiometric amounts of the SiH and alkenyl functionalities. Thus, instead of the conventional 10-20 percent molar excess of the alkenyl polyether, the hydrosilylation synthesis step of the instant invention can be done with essentially no molar excess of alkyl branched, unsaturated polyether. SiH/alkenyl stoichiometry in the range 0.99-1.09 is effective. Treatment of the polyether with ascorbic acid and ascorbates as taught in U.S. Pat. No. 5,986,122 improves hydrosilylation reactivity and permits use of reduced Pt catalyst levels. The relevant teachings of this patent are also incorporated herein by reference.

The polymers of the present invention form a clear, transparent homogeneous single-phase solution that can be cured directly without employing any additional homogenizing solvents, depending on the molecular weight of the present siloxane monomers, which are miscible with hydrophilic hydrogel monomers. Calculated solubility parameter values based on Fedors method (Robert F. Fedors, *Polymer Engineering and Science*, February 1974; vol. 14, No. 2) for the present inventive monomers range from approximately 16.5 to approximately 19 $(J/mol)^{1/2}$, which is closer to the solubility parameter value of conventional hydrogel monomers (such as HEMA, NVP and DMA) than silicone monomers such as TRIS. Miscibility is realized if the difference in solubility parameter between the instant inventive monomers and the hydrophilic co-monomers is less than about 7.7 $(J/mol)^{1/2}$.

In another embodiment of the present invention, the polymers may be formed into silicone-hydrogel films, via processes known in the art. The silicone-hydrogel films of the present invention are soft, flexible and highly transparent. Silicone-hydrogel films made from the inventive monomers exhibit better surface wettability and oxygen permeability compared to ones made using monomers having linear alkyl linked methacrylated silicone polyether chains, The present silicone hydrogel films were found to have dynamic advancing contact angles with water, in the range of 80° to 30° and absorb about 10 to 60 wt. % of water, which can vary depending on the molecular weight of the polyethers. The silicone hydrogels produced were also found to have good mechanical properties (such as low modulus and high tear strength) required for the contact lens application.

Conventional silicone-hydrogel films are generally produced by curing a mixture of hydrophobic silicone monomers and hydrophilic hydrogel monomers in the presence of about 10 to 40 wt. % of solvent, as they are incompatible with each other. However in the current invention, the inventive methacrylated silicone monomers are found to be miscible with conventional hydrophilic hydrogel monomers (such as HEMA, NVP and DMA) and can form a homogeneous solution suitable to produce silicone-hydrogel films without employing any solvent.

The densities of the present monomers generally range from 0.89-1.1 g/cm³ at 25° C. and the refractive index range from 1.4-1.46 for the sodium D line. The instant inventors have found that monomers with refractive index greater than 1.431 and density greater than 0.96 g/cm³ produce completely miscible compositions or pseudo miscible compositions that appear homogeneous, clear and transparent with hydrophilic monomers like HEMA, in the absence of compatibilizing solvents. As has been stated above, conventional silicone monomers (for example, TRIS) must be mixed with hydrophilic monomers like HEMA in the presence of a solvent to get miscible compositions to make silicone hydrogels. The hydrogel co-monomer used to make silicone-hydrogel copolymers of the present invention can be hydrophilic acrylic monomers such as HEMA, Dimethylacrylamide (DMA), N-Vinyl pyrollidone (NVP), Methacrylic acid (MA) etc.

In the present invention, the resulting polymers may be formed into silicone-hydrogel films, via processes known in the art. Accordingly, the present invention is also directed to contact lens produced from either homo or copolymers of the present invention. The monomers/polymers of the present invention can be formed into contact lenses by spincasting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

The relative softness or hardness of the contact lenses fabricated from the resulting polymer of this invention can be varied by decreasing or increasing the molecular weight of the polysiloxane prepolymer end-capped with the activated unsaturated group (such as methacryloxy) or by varying the percent of the co-monomer. Generally, as the ratio of polysiloxane units to end-cap units increases, the softness of the material increases.

The polymers of this invention may also contain ultraviolet absorbents, pigments and colorants in the form of additives or co-monomers.

As stated above, the silicone-hydrogels of the present invention exhibit higher oxygen transport with improved surface wettable properties when compared to silicone-polyether copolymers having linear alkyl linking groups. The monomers and prepolymers employed in accordance with this invention are readily polymerized to form three-dimensional networks, which permit the transport of oxygen with improved wettability along with better mechanicals and optical clarity.

For example, the silicone hydrogel film produced with 69 wt % of a monomer of the current invention and 29 wt % of HEMA co-monomer shows higher oxygen permeability (360 Barrer) with lower captive bubble contact angle (40°) and low modulus (0.8 MPa) as against the silicone hydrogel film produced with corresponding silicone-polyether having linear alkyl linking groups, which shows oxygen permeability of 266 Barrer, captive contact angle of 58° and modulus >2 MPa for similar composition with HEMA. Similar trends were observed for silicone-hydrogels produced with different compositions of HEMA and the inventive monomer.

Specific use of the films include intraocular contact lenses, artificial corneas, and soft disposable long-wear contact lenses or as coatings for biomedical devices.

EXAMPLES

The following Examples are illustrative only and should not be construed as limiting the invention, which is properly delineated in the appended claims. Methacrylated silicone polyether monomers having varying ethylene oxide (EO) content were produced using methallyl (branched) polyethers having different EO chain lengths following the synthesis scheme disclosed in Example 1. For comparison purposes, following the same scheme, methacrylated silicone polyether having linear alkyl linking groups were prepared using allyl (linear) polyethers with similar EO chain lengths. The methacrylated siloxane monomers were separately copolymerized with conventional hydrogel monomer with different weight ratios to produce silicone hydrogel films. The properties of silicone-hydrogel films obtained with methacrylated silicone polyether monomers having branched linking group were compared against those of silicone-hydrogel films prepared from linearly linked methacrylated silicone polyether monomers. As shown in the examples, emphasis is given to those properties considered to be critical to contact lens manufacture, use and comfort. The properties of the films obtained with monomers of the current invention having branched alkyl-linking groups were found to desirably superior to those from the films prepared with monomers having linear alkyl-linking groups.

The silicone-hydrogel films produced were evaluated for lens properties using the following methods.

(1). Equilibrium Water Content

The film was immersed in deionized water for 48 hours. Then the surface water was wiped off gently using lintless tissue paper. The hydrated film was weighed precisely and then dried in an oven at 37° C. for 48 hours and weighed again for dry weight. Water content was calculated based on weight change using the following equation.

$$\% \text{ Water content} = \frac{\text{Weight of hydrated lens} - \text{Weight of dry lens}}{\text{Weight of hydrated lens}} \times 100$$

(2). Water Wettability (Measured according to: Neumann A W, Godd R J. Techniques of measuring contact angles. In: Good R J, Stromberg R R, Editors. Surface and Colloid science—Experimental methods, vol. 11. New York: Plenum Publishing; 1979. pp. 31-61.)

Water wettability of the film surface was evaluated by measuring contact angle using both a dynamic contact angle method and a captive air bubble method with a Ramé Hart NRL C.A. goniometer. In the dynamic contact angle method the wet films were first pressed with lintless tissue paper and then a drop of water was placed on the surface. The contact angle was measured with respect to time using a goniometer. In the captive bubble method, which better simulates the on eye conditions, an air bubble injected from a syringe is brought into contact with the film immersed in Milli-Q water and the contact angle is then measured. Lower contact angle values represent a greater degree of hydrophilicity or better surface wettability of the film.

(3) Oxygen Permeability (Dk Value)

(Measured according to: V. Compan, et al., *Oxygen Permeability of Hydrogel Contact Lenses with Organosilicon Moieties, Biomaterials*, vol 23 (2002, #13) pp 2767-2772.)

Oxygen permeability is one of the important factors in contact lens performance. Generally, the higher the permeability the more desirable the material. The oxygen permeability (Dk) for these samples was measured using polarographic technique following ISO 9913 standards method. The film was clamped into the permeation cell and the donor chamber was filled with oxygen saturated PBS (phosphate buffered saline). The concentration of oxygen in the receptor cell was monitored, and plotted as a function of time and the permeability was determined from the initial slope of the plot.

(4) Modulus

The Young's modulus of the hydrated film was measured using an Instron tensile tester. The wet samples were cut into 6 cm×0.8 cm strips and the mechanical properties were measured with a load cell of 50 N and crosshead speed of 10 mm/minute. The modulus was determined from the initial slope of a stress-strain curve. Modulus is directly correlated to the softness of the material. Lower the modulus, softer the material.

MONOMER PREPARATION

Example 1

Synthesis of Compound Represented by the Formula

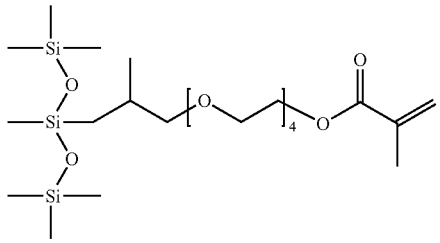

The methacrylated silicone-polyether monomers were prepared using a two-step process. In a first step, a hydrosilylation reaction occurs between hydroxyl terminated methallyl polyether and mono-hydride functional trisiloxane moiety. In the second step, the hydroxyl group is converted into the polymerizable methacrylate group through a methacrylation reaction In a specific process, heptamethyl-trisiloxane (70 g) and a methallyl-terminated polyethylene glycol, having an average of four ethylene oxide (EO) units in the chain, (75 g) were introduced into a 500 mL three-neck round bottom (RB) flask equipped with a reflux condenser, mechanical stirrer, temperature controller with thermocouple and a nitrogen inlet. The contents were heated to 80° C.-85° C. in the presence of Karstedt's catalyst (platinum complex of 1,3-divinyltetramethyldisiloxane, 30 ppm Pt based on weight of total reactants charged) and 50 ppm sodium propionate buffer (see U.S. Pat. No. 4,847,398) to prevent side reactions like dehydrocoupling reaction from taking place. After completion of the hydrosilylation, volatile compounds (for example, toluene introduced with the catalyst) were distilled (stripped) under reduced pressure. The final product, hydroxyl terminated silicone polyether, was obtained as a colorless, transparent liquid in quantitative yield without any undesired side products. The resultant pure product was well characterized by multinuclear NMR ($^1H$, $^{13}C$, $^{29}Si$) spectroscopy and gel permeation chromatography (GPC). Synthesis of the silicone polyethers of the present invention can occur with or without solvent. If solvents are used, preferred ones include toluene, isopropyl alcohol or methyl ethyl ketone.

Next, the silicone polyether (142 g) that was synthesized in the step above, triethylamine (30.3 g) (or alternatively basic ion-exchange resin acid scavenger), and methyl ethyl ketone (250 ml) were introduced into a three-neck one liter RB flask equipped with dropping funnel and a stirring blade. The flask was immersed in an ice bath and methacryloyl chloride (31.3 g) was added drop wise over a period of approximately 1 hour with constant stirring. After completion of the addition, the stirring was continued for another 3 hours at room temperature. The triethylamine hydrochloride salt thus formed precipitated out during the reaction. When the ion exchange resin was used, it was filtered off. The solvent was removed with a rotary vacuum evaporator and the final monomer was obtained as a colourless, transparent liquid. The low boiling point of the solvent used enabled the solvent to be removed completely at a temperature of about 30° C. to 40° C. under vacuum (i.e. less than about 10 mm Hg). The resulting hydrophilic monomer product was colorless to pale yellow. It was stored in amber bottle in a refrigerator. Characterization by infrared spectroscopy, multinuclear NMR ($^1H$, $^{13}C$, $^{29}Si$) spectroscopy and GPC followed.

The proton and silicon NMR results of the final monomer are shown below.

$^1H$-NMR (ppm): 0.07 (($CH_3$)Si—), 0.26, 0.56 (Si—$CH_2$—), 0.95 (—$CH_3$), 1.93 (=C($CH_3$)), 3.64 (—$CH_2CH_2O$—), 4.29 ($CH_2COO$), 5.56, 6.12 (=$CH_2$)

$^{29}Si$—NMR (ppm): −22 (—OSi($CH_3$)(EO)), 7 (—OSi($CH_3$)$_3$)

Example 2

Synthesis of Compound Represented by the Formula

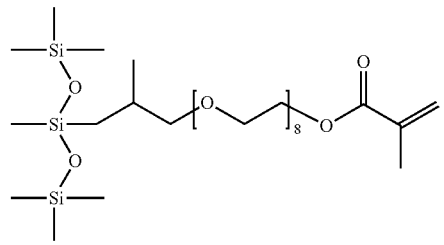

This monomer was obtained in the same way as in Example 1 except that methallyl terminated polyethylene glycol having an average of 8 EO units was used instead of 4 EO units. The SiH/alkenyl stoichiometry was 1.05.

Example 3

This example illustrates synthesis of the methacrylated siloxane-polyether of Example 2 with the following changes. (1) Ascorbate treatment of the polyether as taught in Example 2T of U.S. Pat. No. 5,986,122. (2) Reduction in Pt usage to 10 ppm, (3) Performing the methacrylate capping at 35-45° C. instead of at 0-5° C., (4) Use of hexane in place of methylethyl ketone, (5) Use of tripropylamine in place of triethylamine and (6) Addition of 50 ppm hydroquinone to a portion of final methacrylated siloxane-polyether product stored at room temperature.

It was observed that precipitation of tripropylamine hydrochloride was complete when hexane was the solvent. No additional salt precipitation was observed when the solvent was stripped in vacuo. Otherwise, the methacrylated siloxane-polyether product obtained showed the same physical and compositional properties as were measured for the product of Example 2.

Formation of Silicon-Hydrogel Films

Example 4

The compound obtained in Example 1 (49 parts by weight), 2-hydroxy ethylmethacrylate (49 parts by weight), ethylene glycol dimethacrylate (EGDMA) (1 part by weight), and Irgacure OXE01 (1 part by weight) were mixed and stirred. The resulting clear, homogeneous and transparent reaction mixture was purged with nitrogen gas and poured into an aluminium pan covered with a polystyrene Petri dish. The thin film of the reaction mixture was exposed to UV radiation in a chamber at 15 mW/cm² for 20 minutes. After curing the film was immersed in isopropyl alcohol and then placed in deionized water for 48 hours. The silicone hydrogel film produced was transparent and absorbed about 18 wt. % of water.

Examples 5-7

A silicone-hydrogel film was obtained in the same way as in Example 4 except that the compound obtained in Example 2 was used instead of compound obtained in Example 1. The final sample was obtained as clear, transparent-thin film and stored in pure water. Table 1 shows the formulations and the properties of the silicone-hydrogel films formed in Examples 5-7.

Comparative Example 1

Synthesis of Compound Represented by the Formula

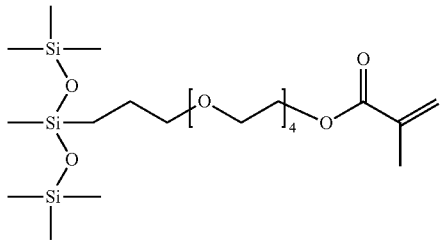

The monomer was prepared in the same way as in Example 1 except that mono allyl terminated polyethylene glycol having an average of 4 EO units was used instead of methallyl polyethylene glycol. The proton NMR of the final monomer shows the presence of hardly separable isomerized polyether along with the monomer, which is not observed with the monomer of the current invention.

The proton and silicon NMR results of the final monomer are shown below.

$^1$H-NMR (ppm): 0.07 ((CH$_3$)Si—), 0.43 (Si—CH$_2$—), 1.58 (—CH$_2$—), 1.93 (=C(CH$_3$)), 3.64 (—CH$_2$CH$_2$O—), 4.28 (CH$_2$COO), 4.36, 4.75, 5.96, 6.23 (due to propenyl group (isomerized polyether)) 5.55, 6.12 (=CH$_2$)

$^{29}$Si—NMR (ppm): -22 (—OSi(CH$_3$)(EO)), 7 (—OSi(CH$_3$)$_3$)

Comparative Example 2

Synthesis of Compound Represented by the Formula

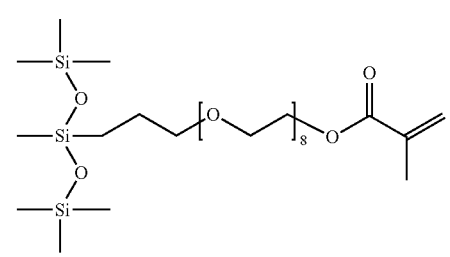

The monomer was prepared in the same way as in comparative example 1 except that mono allyl terminated polyethylene glycol having an average of 8 EO units was used instead of methallyl polyethylene glycol.

Comparative Example 3

A silicone-hydrogel film was obtained in the same way as in Example 4 except that the compound obtained in 'Comparative example 1 (49 parts by weight) was used instead of the compound obtained in Example 1. The final transparent sample was stored in deionized water.

Comparative Examples 4-6

A silicone-hydrogel film was obtained in the same way as in comparative Example 3 except that the compound obtained in 'Comparative example 2' was used instead of the compound obtained in Comparative example 1. The final transparent sample was stored in deionized water. Table 1 shows the formulations and the properties of the silicone-hydrogel films formed in comparative examples 4-6.

Comparative Example 7

Synthesis of Compound Represented by the Formula

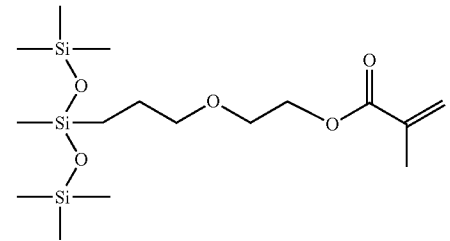 [SMILES: C=C(C)C(=O)OCCOCCC[Si](C)(O[Si](C)(C)C)O[Si](C)(C)C]

The monomer was prepared in the same way as in comparative example 1 except that, low molecular weight, allyl oxy ethanol was used instead of polyethylene glycol.

TABLE 1

Properties of Contact Lens Films made from the Silicone Monomer of Example 2 and Comparative Example 2

|  | Ex 5 | Ex 6 | Ex 7 | CEx 4 | CEx 5 | CEx 6 |
|---|---|---|---|---|---|---|
| Composition (wt. %) | | | | | | |
| Silicone monomer (Ex 2) | 49 | 59 | 69 | 0 | 0 | 0 |
| Comparative silicone monomer (CEx 2) | 0 | 0 | 0 | 49 | 59 | 69 |
| HEMA | 49 | 39 | 29 | 49 | 39 | 29 |
| EGDMA | 1 | 1 | 1 | 1 | 1 | 1 |
| Irgacure * | 1 | 1 | 1 | 1 | 1 | 1 |
| Properties | | | | | | |
| Equilibrium water content (%) | 30 | 26 | 23 | 28 | 25 | 21 |

TABLE 1-continued

Properties of Contact Lens Films made from the Silicone Monomer of Example 2 and Comparative Example 2

|  | Ex 5 | Ex 6 | Ex 7 | CEx 4 | CEx 5 | CEx 6 |
|---|---|---|---|---|---|---|
| Dynamic contact angle (at 3 minutes) | 42° ± 4° | 38° ± 4° | 35° ± 4° | 50° ± 4° | 48° ± 4° | — |
| Captive bubble contact angle | 40° ± 3° | 38° ± 3° | 38° ± 3° | 47° ± 5° | 52° ± 4° | 58° ± 3° |
| Young's modulus [MPa] | 0.8 ± 0.3 | 0.4 ± 0.1 | 0.4 ± 0.1 | >2 | 1 ± 0.3 | 0.8 ± 0.1 |
| Oxygen permeability (Dk) [Barrer] | 305 ± 10 | — | 360 ± 10 | 240 ± 8 | — | 266 ± 10 |

* Photoinitiator available from Ciba Specialty Chemicals

Table 1 demonstrates that the silicone-hydrogel films produced using the branched silicone monomer (Ex. 5-7) shows higher oxygen permeability with lower water contact angles, hence improved wettability, and lower modulus properties compared to silicone-hydrogel films produced with corresponding formulations of linear siloxane monomer (CEx. 4-6). Unexpectedly, decreases in contact angle and modulus were observed with increasing siloxane content in the silicone-hydrogel films produced with silicone-polyether monomer having both linear and branched alkyl linking groups.

Table 2 discloses the refractive index (RI), density and solubility parameters obtained for the different monomers. The solubility parameter values of the claimed methacrylated silicone polyethers and other monomers were calculated using group contribution method based on "Fedors method" (see paragraph 36). With increasing number of EO units in the monomers, the RI and density of the monomers increase and equal that of a high RI monomer like HEMA. These increases contribute to better miscibility between the siloxane and hydrogel monomers and formation of transparent, homogeneous, stable silicone-hydrogel compositions that can be cured directly without using any solvent for compatibles.

silicone monomers to select miscible or immiscible behavior with polar organic monomers such as HEMA is achieved by selecting the ratio of low polarity silicone group to more polar polyether groups. Further selection of the type and size of the polyether groups in part determines the interaction with water in a hydrogel formed from the silicone monomer, organic monomers and other materials of a contact lens formulation.

The methacrylated silicone polyether monomers of the current invention with equal to or greater than 3 EO units on mixing with 50 wt. % of HEMA monomer, immediately form a uniform clear homogeneous transparent solution. Methacrylated silicone polyether monomers with one or no EO units on mixing with 50 wt. % of HEMA monomer form two layers, which upon vigorous shaking produces a hazy or turbid solution. The data in Table 2 show that for monomers with a calculated solubility parameter of about 16.5 $(J/mol)^{1/2}$, only partial miscibility with HEMA is observed in a 50:50 wt. % mixture. If the solubility parameter of the silicone monomer is about 17 $(J/mol)^{1/2}$ or above, then it is miscible with HEMA in a 50:50 wt. % mixture. The calculated solubility parameter value for TRIS is 15.8 $(J/mol)^{1/2}$ and the prediction for a 50:50 wt. % mixture of TRIS (tris

TABLE 2

Physical properties of the monomers and their miscibility with organic co-monomers (HEMA, DMA, NVP)

| Monomer | No of EO units in monomer | Refractive index | Density [g/ml] | Solubility Parameter $(J/mol)^{1/2}$ | Miscibility with comonomer | Copolymer appearance |
|---|---|---|---|---|---|---|
| HEMA | — | 1.454 | 1.079 | 24.65 | — | — |
| DMA | — | 1.473 | 0.962 | 21.66 | — | — |
| NVP | — | 1.512 | 1.04 | 25.31 | — | — |
| Ex 1 | 4 | 1.441 | 0.975 | 17.02 | Miscible | Transparent |
| Ex 2 | 8 | 1.448 | 1.012 | 17.5 | Miscible | Transparent |
| C Ex 1 | 4 | 1.443 | 1.000 | 17.10 | Miscible | Transparent |
| C Ex 2 | 8 | 1.450 | 1.007 | 17.58 | Miscible | Transparent |
| C Ex 7 | 1 | 1.431 | 0.962 | 16.50 | Poor Miscibility | Opaque |
| TRIS | 0 | 1.395 | 0.918 | 15.8 | Not Miscible - Predicted | Opaque |

TRIS = Tris(trimethylsiloxy)silyl)propyl methacrylate

The data in Table 2 illustrate that as the number of EO units increases in the methacrylated silicone monomer the RI, density and solubility parameter increase and this helps to form transparent and miscible silicone hydrogel compositions with various organic comonomers before and after curing. A difference in solubility parameter of less than or equal to 7.7 $(J/mol)^{1/2}$ between co-monomer and the methacrylated polyether-silicone copolymer indicates miscibility.

The data in Table 2 also illustrate a key aspect of the invention in the control of miscibility phenomena through control of molecular structure. Control of the structure of (trimethylsiloxy)silyl)propyl methacrylate) with HEMA, based on calculated solubility parameter, is an immiscible composition.

While the invention has been described with reference to a preferred embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. A hydrogel composition comprising a silicone-containing monomer having the general formula:

or

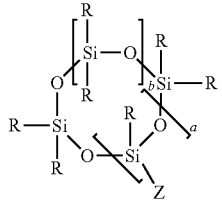

wherein
a is 1 to about 50;
b is 0 to about 100;
each R is independently selected from the group consisting of monovalent aliphatic, cycloaliphatic or aromatic hydrocarbon groups of 1 to about 10 carbons and halogenated hydrocarbon groups of 1 to about 10 carbons;
Z is a polyether having the general formula:

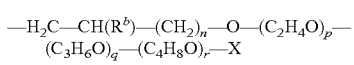

wherein
n is 1 to about 20;
p and q individually are 0 to about 100;
$R^b$ is an alkyl group having from 1 to about 4 carbon atoms;
r is 0 to about 50 and the sum of p+q+r is greater than 0; and
X is a polyether-capping group having the general formula:

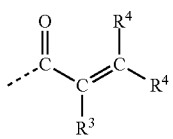

wherein $R^3$ and $R^4$ independently are either hydrogen or a substituted or unsubstituted saturated monovalent hydrocarbon group of 1 to about 20 carbons.

2. The hydrogel composition of claim 1, wherein at least one R comprises a fluorinated hydrocarbon or trialkylsilyloxy group.

3. The hydrogel composition of claim 1, wherein each R independently comprises a saturated monovalent hydrocarbon group of from 1 to 6 carbon atoms or a phenyl group.

4. The hydrogel composition of claim 1, wherein a+b is 1 to about 20 for formula (I) and 3 to about 20 for formula (II).

5. The hydrogel composition of claim 1, wherein the silicone-containing monomer comprises a cyclic monomer.

6. The hydrogel composition of claim 1, wherein the silicone-containing monomer has the following formula:

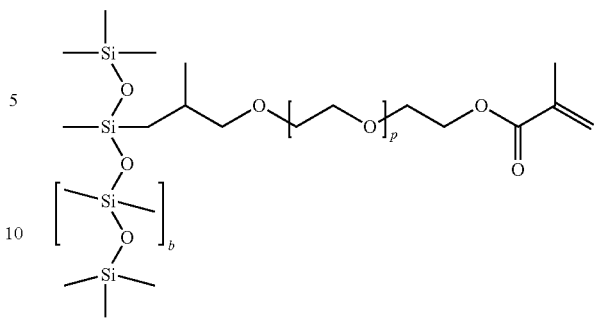

wherein b is 0 to about 100, and p is 1 to about 50.

7. The hydrogel composition of claim 6, wherein b is from 0 to 2 and p is from 2 to about 15.

8. The hydrogel composition of claim 1, wherein b is equal to 0 and the total number of carbon atoms present in Z is at least 6.

9. The hydrogel composition of claim 1, wherein n is from 1 to 3 and $R^b$ is a methyl group.

10. The hydrogel composition of claim 1, wherein the composition comprises monomers of the silicone-containing monomer having the same structure.

11. The hydrogel composition of claim 1 comprising the silicone-containing monomer and a second silicone-containing monomer of the Formula (I), and the silicone-containing monomer has a different structure than the second silicone-containing monomer.

12. The hydrogel composition of claim 1 comprising the silicone-containing monomer and at least one hydrophilic monomer.

13. The hydrogel composition of claim 12, wherein the at least one hydrophilic monomer is chosen from a vinylic monomer, an acrylamide monomer, an acrylic monomer, or a combination of two or more thereof.

14. The hydrogel composition of claim 12, wherein the at least one hydrophilic monomer is chosen from N-vinyl-pyrolidone, 2-hydroxy-ethyl-methacrylate, N,N-dimethylacrylamide, methacrylic acid, or a combination of two or more thereof.

15. The hydrogel composition of claim 12, wherein the at least one hydrophilic monomer is a multifunctional crosslinker.

16. The hydrogel composition of claim 12 wherein the ratio of the silicone-containing monomer to the at least one hydrophilic monomer is from 1:100 to about 100:1.

17. A hydrogel film prepared from the hydrogel forming composition of claim 12.

18. A hydrogel composition comprising (a) a silicone-containing monomer, and (b) at least one hydrophilic co-monomer, wherein the difference in solubility parameter between the silicone-containing monomer and the at least one hydrophilic co-monomer is less than about 7.7 $(J/mol)^{1/2}$, and the silicone-containing monomer is of the formula:

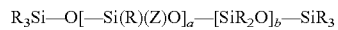

or

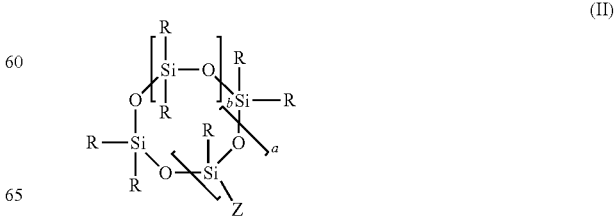

wherein
a is 1 to about 50;
b is 0 to about 100;
each R is independently selected from the group consisting of monovalent aliphatic, cycloaliphatic or aromatic hydrocarbon groups of 1 to about 10 carbons and halogenated hydrocarbon groups of 1 to about 10 carbons;
Z is a polyether having the general formula:

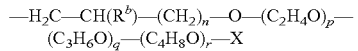
—$H_2C$—$CH(R^b)$—$(CH_2)_n$—O—$(C_2H_4O)_p$—$(C_3H_6O)_q$—$(C_4H_8O)_r$—X wherein
n is 1 to about 20;
p and q individually are 0 to about 100;
$R^b$ is an alkyl group having from 1 to about 4 carbon atoms;
r is 0 to about 50 and the sum of p+q+r is greater than 0; and
X is a polyether-capping group having the general formula:

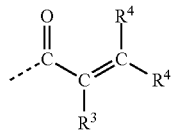

wherein $R^3$ and $R^4$ independently are either hydrogen or a substituted or unsubstituted saturated monovalent hydrocarbon group of 1 to about 20 carbons.

19. The hydrogel composition of claim 18, wherein the silicone-containing monomer has the formula

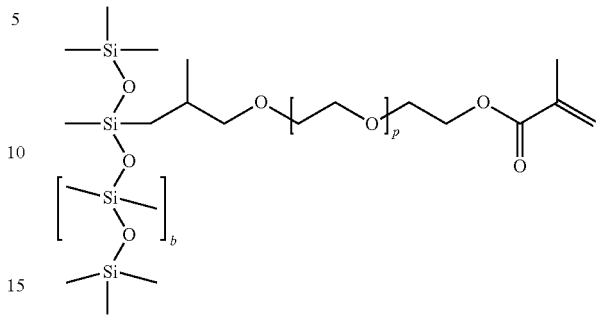

wherein b is 0 to about 100, and p is 1 to about 50; and the at least one hydrophilic co-monomer is chosen from N-vinyl-pyrolidone, 2-hydroxy-ethyl-methacrylate, N,N-dimethylacrylamide, methacrylic acid, or a combination of two or more thereof.

20. The hydrogel composition of claim 18, wherein the composition is free of a solvent.

21. A hydrogel film prepared from the composition of claim 18.

22. A contact lens comprising the hydrogel composition of claim 1.

* * * * *